(12) United States Patent
Myllyoja et al.

(10) Patent No.: US 10,315,966 B2
(45) Date of Patent: Jun. 11, 2019

(54) UPGRADING 5-NONANONE

(71) Applicant: NESTE OYJ, Espoo (FI)

(72) Inventors: Jukka Myllyoja, Vantaa (FI); Mats Käldström, Porvoo (FI); Marina Lindblad, Helsinki (FI); Jarno Kohonen, Kerava (FI); Maaria Seläntaus, Helsinki (FI); Elias Ikonen, Espoo (FI)

(73) Assignee: NESTE OY, Espoo (FI)

( * ) Notice: Subject to any disclaimer, the term of this patent is extended or adjusted under 35 U.S.C. 154(b) by 0 days.

(21) Appl. No.: 15/707,760

(22) Filed: Sep. 18, 2017

(65) Prior Publication Data
US 2018/0086677 A1 Mar. 29, 2018

(30) Foreign Application Priority Data

Sep. 29, 2016 (EP) .................................. 16191277

(51) Int. Cl.
*C07C 1/207* (2006.01)
*C07C 5/03* (2006.01)
*C10L 1/04* (2006.01)
*C07C 45/74* (2006.01)
*C10G 45/02* (2006.01)
(Continued)

(52) U.S. Cl.
CPC .......... *C07C 1/2074* (2013.01); *B01J 23/892* (2013.01); *B01J 27/185* (2013.01); *B01J 29/85* (2013.01); *C07C 1/2076* (2013.01); *C07C 5/03* (2013.01); *C07C 5/2702* (2013.01); *C07C 45/74* (2013.01); *C10G 3/42* (2013.01); *C10G 3/50* (2013.01); *C10G 45/02* (2013.01); *C10G 45/32* (2013.01); *C10G 50/00* (2013.01); *C10G 65/04* (2013.01); *C10G 65/043* (2013.01); *C10L 1/04* (2013.01); *B01J 21/00* (2013.01); *C07C 2521/06* (2013.01); *C07C 2523/04* (2013.01); *C07C 2523/10* (2013.01); *C07C 2523/883* (2013.01); *C07C 2531/10* (2013.01); *C10G 2300/202* (2013.01); *C10G 2400/02* (2013.01);
(Continued)

(58) Field of Classification Search
CPC combination set(s) only.
See application file for complete search history.

(56) References Cited

U.S. PATENT DOCUMENTS

2009/0255171 A1 10/2009 Dumesic et al.
2010/0312028 A1* 12/2010 Olson ..................... C10L 1/08
585/242

(Continued)

FOREIGN PATENT DOCUMENTS

FR 2 849 052 A1 6/2004
WO WO 2009/045156 A1 4/2009
(Continued)

OTHER PUBLICATIONS

European Search Report dated Mar. 6, 2017, issued by the European Patent Office in the corresponding European Patent Application No. EP 16 19 1277. (8 pages).

*Primary Examiner* — Ellen M McAvoy
*Assistant Examiner* — Chantel L Graham
(74) *Attorney, Agent, or Firm* — Buchanan Ingersoll & Rooney PC

(57) ABSTRACT

Provided are fuel components, a method for producing fuel components, use of the fuel components and fuel containing the fuel components based on 5-nonanone.

16 Claims, 2 Drawing Sheets

(51) Int. Cl.
*C10G 45/32* (2006.01)
*C10G 50/00* (2006.01)
*C10G 65/04* (2006.01)
*C10G 3/00* (2006.01)
*C07C 5/27* (2006.01)
*B01J 23/89* (2006.01)
*B01J 27/185* (2006.01)
*B01J 29/85* (2006.01)
*B01J 21/00* (2006.01)

(52) U.S. Cl.
CPC ..... *C10G 2400/04* (2013.01); *C10G 2400/08* (2013.01); *C10L 2200/0469* (2013.01); *Y02P 30/20* (2015.11)

(56) References Cited

U.S. PATENT DOCUMENTS

| | | |
|---|---|---|
| 2010/0317898 A1 | 12/2010 | Noziere et al. |
| 2010/0324310 A1 | 12/2010 | Dumesic et al. |
| 2011/0277375 A1 | 11/2011 | Chheda et al. |
| 2012/0186144 A1* | 7/2012 | Truitt ............... C07C 41/09 44/448 |
| 2013/0017590 A1 | 1/2013 | Chung et al. |

FOREIGN PATENT DOCUMENTS

| | | |
|---|---|---|
| WO | WO 2010/151343 A1 | 12/2010 |
| WO | WO 2011/115394 A2 | 9/2011 |
| WO | WO 2011/143392 A1 | 11/2011 |

\* cited by examiner

UPGRADING 5-NONANONE

TECHNICAL FIELD

The present invention relates to upgrading 5-nonanone. Specifically, the invention relates to fossil and/or renewable fuel components, a method for producing fossil and/or renewable fuel components, use of the fuel components and fuel containing the fuel components. In particular, the present invention relates to fuel components based on 5-nonanone (dibutylketone) and derived from renewable sources.

TECHNICAL BACKGROUND

The production of fuel components from renewable sources is of increasing interest in view of greenhouse gas production when using conventional fuel, i.e. fossil fuel or a mixture of fossil fuel components and renewable fuel components other than the ketone. Therefore, various methods for upgrading renewable material so as to be suitable for use in fuel have been studied in the art. Many of these methods employ large amounts of hydrogen gas in order to convert the oxygen-containing renewable material into hydrocarbon compositions suitable for fuel applications. However, since hydrogen gas is mainly produced from fossil sources, there still is desire for improvement regarding methods employing less hydrogen gas while yet providing high quality fuel components.

5-nonanone can be produced from various renewable sources. For example, the most common way of producing 5-nonanone from levulinic acid (LA) is the conversion of LA to γ-valerolactone (GVL), subsequent conversion of GVL to pentanoic acid (PA), which is then converted to 5-nonanone.

5-nonanone shows several advantages as an intermediate in the production of fuel components. 5-nonanone spontaneously separates from water so that no expensive separation process needs to be employed. Furthermore, 5-nonanone can be produced from pentanoic acid via ketonisation, which method does not require the addition of hydrogen but nevertheless significantly reduces the oxygen content of the bio-derived material. In the ketonisation reaction, the oxygen is removed in the form of carbon dioxide and water. However, the prior art still faces problems regarding selectivity and conversion rate in the production of 5-nonanone. Accordingly, processes for producing 5-nonanone from renewable sources in industrial scale and high selectivity and conversion rate are highly desired.

Prior art relating to the production of 5-nonanone and the production of fuel components and other chemicals via 5-nonanone is known in the art.

It is known that 5-nonanone can be produced from LA via GVL and pentanoic acid. The pentanoic acid can then be converted to 5-nonanone over Pd/Nb$_2$O$_5$. Unreacted pentanoic acid is the major impurity in the product 5-nonanone i.e. dibutylketone (DBK). The boiling points of 5-nonanone and pentanoic acid are very similar, so that separation of these two compounds using simple distillation methods is difficult. A series of flash separation and distillation as well as optional extraction using methanol may be used to obtain a purity of 90% or more. However, this technique requires large scale distillation and consumes much energy. Accordingly, there is still need for methods to produce 5-nonanone using a simplified and less energy consuming method.

Ketonisation of pentanoic acid to 5-nonanone, followed by hydrogenation to provide nonanol and optional oligomerization of an alkene such as non-4-ene derived from nonanol to produce hydrocarbon compositions is also known.

WO 2010/151343 A1 discloses ketonisation of pentanoic acid to 5-nonanone and use of 5-nonanone as a precursor for fuel applications.

SUMMARY OF THE INVENTION

The present invention is defined in the independent claims. Further beneficial embodiments are set forth in the dependent claims. Specifically, the present invention relates to one or more of the following items:

1. A method for producing fuel components, the method comprising
    a preparation step of providing a feedstock comprising at least 5 wt.-% of 5-nonanone, and
    a condensation step of condensing at least the 5-nonanone in the feedstock in the presence of a condensation catalyst to obtain a condensation product.

The reaction of the present invention provides a compound (or mixture of compounds each) having a large number of carbon atoms (usually in the range of 13 to 18) and a low oxygen content which makes it suitable as a fuel component and/or as a fuel component precursor. Further, since this reaction consumes no hydrogen gas, the product can be obtained using only a minimum of hydrogen gas which is commonly produced exclusively from fossil sources. Therefore, the present invention contributed to greenhouse-gas saving.

In the present invention, the term "upgrading" means modifying and/or refining a component by a chemical reaction so that it can be used as a fuel component.

2. The method according to item 1, wherein the feedstock comprises at least 7 wt.-% of 5-nonanone, preferably at least 10 wt.-% of 5-nonanone, more preferably at least 15 wt.-% of 5-nonanone, at least 20 wt.-% of 5-nonanone, at least 30 wt.-% of 5-nonanone, at least 40 wt.-% of 5-nonanone, at least 50 wt.-% of 5-nonanone, at least 60 wt.-% of 5-nonanone, at least 70 wt.-% of 5-nonanone, at least 80 wt.-% of 5-nonanone, at least 90 wt.-% of 5-nonanone, or at least 95 wt.-% of 5-nonanone.

The method of the present invention may be carried out using high contents of 5-nonanone and may even be carried out using only 5-nonanone as the feedstock, so that the amount of impurities generated by side reactions with additional components of the feedstock can be minimized.

3. The method according to item 1 or 2, wherein no hydrogenation is carried out in the condensation step. For example, in this embodiment, no hydrogen gas is added in the condensation step.

In the method of the present invention, which is described in greater detail below, the 5-nonanone is subjected to a condensation reaction, which results in a further decrease of the oxygen content of the molecules involved in the reaction. Thus, a highly oxygen-deficient product can be obtained without the need for additional or simultaneous hydrogenation.

4. The method according to any one of items 1 to 3, wherein the condensation catalyst is
    i) an ion-exchange resin catalyst, preferably an acidic ion-exchange resin catalyst,
    ii) an acid or a base catalyst selected from the group of a metal oxide catalyst, a metal hydroxide catalyst, a metal alkoxide catalyst, metal carbonate catalyst or a metal phosphate catalyst, or
    iii) a mixed metal oxide catalyst or a supported metal oxide catalyst.

These catalysts have shown to provide good activity and high suitability for the method of the present invention.

5. The method according to any one of items 1 to 4, wherein the condensation step is carried out under flow of a carrier gas, such as nitrogen, hydrogen, carbon dioxide, methane or water.

In this embodiment of item 5, the carrier-gas is a gas which does not react with the feedstock or with the product of the condensation step. Specifically, the hydrogen gas in this embodiment is used exclusively as a carrier, not a reactant. In other words, the reaction conditions in the condensation step are such that no hydrogenation reaction occurs, although hydrogen gas is present in the reaction mixture.

6. The method according to any one of items 1 to 5, further comprising a hydrogenation step of hydrogenating the condensation product to obtain a hydrogenated condensation product.

Although the condensation product already has a low oxygen content, it may be desirable to produce e.g. a hydrocarbon composition, i.e. a composition essentially consisting of hydrocarbons and containing no oxygenates (except for impurities). Therefore, the condensation product may be further treated by hydrogenation. Since the condensation product already has a very low oxygen content, the hydrogenation reaction requires only low amounts of hydrogen gas so that e.g. a hydrocarbon composition suitable as a fuel can be obtained using only low amounts of hydrogen gas.

7. The method according to item 6, wherein the hydrogenated condensation product is a hydrocarbon composition, preferably an alkane or a mixture of alkanes.

Hydrocarbon compositions are highly suited as fuel components. Specifically, since conventional fuels comprise mainly hydrocarbons, the hydrocarbon compositions obtainable by the method of the present invention can be blended with conventional fuel components in broad ranges and may even be directly used as a fuel, e.g. as a diesel fuel, a gasoline fuel or a jet fuel.

Specifically, the fuel of present invention may be a mixture of compounds, in which the main components, preferably 50 vol-% or more, are hydrocarbons containing 4 to 25 carbon atoms. Diesel fuel may be a mixture of compounds, in which the main components, preferably 50 vol-% or more, are hydrocarbons containing 11 to 25 carbon atoms. Jet fuel may be a mixture of compounds, in which the main components, preferably 50 vol-% or more, are hydrocarbons containing 9 to 16 carbon atoms. Gasoline may be a mixture of compounds, in which the main components, preferably 50 vol-% or more, are hydrocarbons containing 4 to 9 carbon atoms.

8. A use of the condensation product obtainable by the method according to any one of items 1 to 5 or of the hydrogenated condensation product obtainable by the method according to item 6 or 7 as a fuel component.

9. A diesel, jet or gasoline fuel blend comprising the condensation product obtainable by the method according to any one of items 1 to 5 or the hydrogenated condensation product obtainable by the method according to item 6 or 7 as a fuel component.

The fuel blend may consist of the above-mentioned fuel component of item 8 or 9 or may be a blend comprising at least the above-mentioned fuel component of item 8 or 9 in addition to at least one of a fossil fuel component and a renewable fuel component.

DETAILED DESCRIPTION OF THE INVENTION

Figure 1:
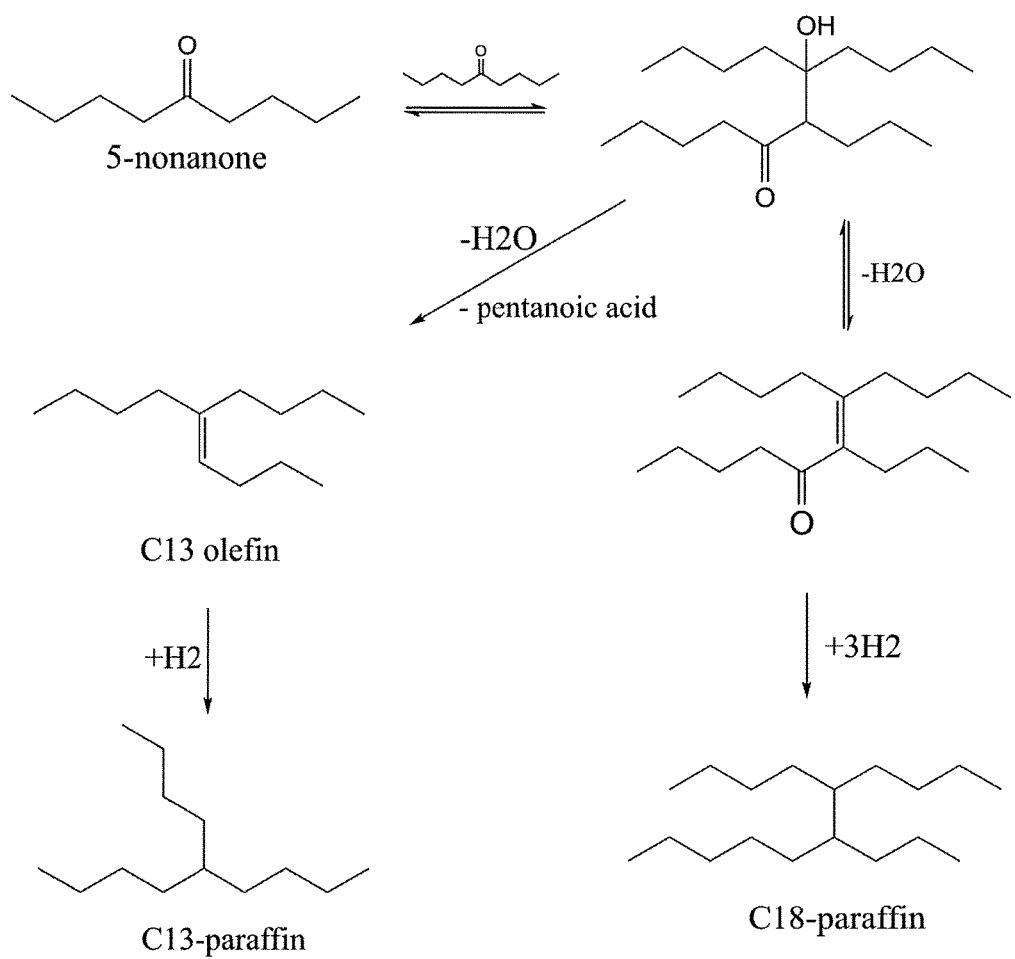
FIG. 1 is a scheme showing a route for the synthesis of hydrocarbon fuel components from 5-nonanone.

Generally, the present invention relates to methods of upgrading 5-nonanone, preferably 5-nonanone from a renewable source, method for the production of fuel components and to fuel containing the upgraded fuel components.

In the following, a detailed description of the invention will be provided step-by-step.

Method for Production of 5-Nonanone

One partial aspect of the present invention relates to the production of 5-nonanone e.g. from a renewable source with high selectivity (preferably more than 95 vol-%) and high conversion (preferably more than 95 vol-%). It is preferred that the 5-nonanone which is upgraded in accordance with the invention be produced using the method disclosed below.

Levulinic acid (LA) is a suitable raw material which can be derived from renewable sources in large quantities in industrial scale.

A schematic reaction route of producing 5-nonanone from LA, which may be employed in the method of the present invention, is as follows:

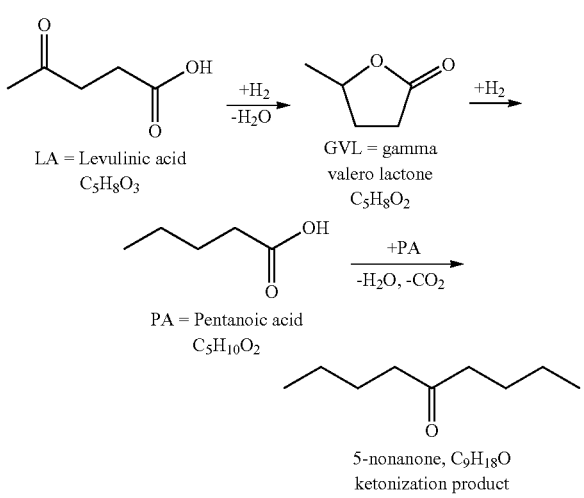

Other ketones may be derived from LA as well, e.g. via carboxylic acid intermediates having 2 to 6 carbon atoms. When using a single type of carboxylic acid e.g. pentanoic acid, a symmetric ketone will be produced. When using two types of carboxylic acids e.g. R1COOH and R2COOH, a mixture of two symmetric ketones (R1C(O)R1 and R2C(O)R2) and one asymmetric ketone (R1C(O)R2) will be formed. If three or more different carboxylic acids are present, a mixture of even more different ketones will be obtained.

Methods for producing pentanoic acid (PA) from LA in reasonable yields are known in the art and any known method for producing pentanoic acid may be employed in the present invention. In one embodiment, LA derived from a renewable source is subjected to hydrogenation to produce GVL. The GVL is subsequently or simultaneously converted to pentanoic acid by hydrogenation. Any suitable catalyst may be used in the hydrogenation reactions, but is preferably a bi-functional catalyst, which contains acid-functionality (having for example zeolites, SAPO or IER as a catalyst component) and metal-functionality (having for example Pt or Pd as a catalyst component) so that ring-opening of GVL to pentenoic acid and hydrogenation of pentenoic acid to PA can proceed simultaneously.

Any other reaction scheme may be employed to produce pentanoic acid, preferably from a renewable source. Further, the reaction scheme is not limited to routes employing LA as a raw material, although this route is preferred.

The prior art discloses several methods for producing 5-nonanone from pentanoic acid. However, none of the prior art techniques achieves both high selectivity and high conversion. Specifically, the known methods achieve a selectivity of at most 90% by weight, wherein the main residue is pentanoic acid (PA). This causes problems in the further procedure. Either, the PA must be separated using complicated methods or the PA leads to side reactions in the subsequent processing.

A preferred 5-nonanone production method of the present invention, however, employs a specific oxide catalyst constituted of an alkali metal oxide and at least one further metal oxide which is different from the alkali metal oxide and achieves almost full conversion of the carboxylic acid to 5-nonanone, preferably more than 95 vol-% relative to all liquid organic reaction products. Accordingly, there is no need for complicated separation techniques which improves the overall energy efficiency of the process.

The oxide catalyst may be a mixed oxide, a solid solution oxide or a catalyst in which one metal oxide is supported on another metal oxide. The alkali metal oxide can be supported on at least one further metal oxide. The oxide catalyst may further be supported on a support other than a metal oxide.

In one embodiment, the alkali metal oxide is $K_2O$, which has shown to provide excellent conversion efficiency. The at least one further metal oxide may be selected from the group consisting of titania, silica, ceria, zirconia and γ-alumina, or mixtures, mixed oxides or solid solutions of these. The at least one further metal oxide may be ceria-zirconia mixed oxide, titania, or a mixture of alumina and titania. In one embodiment, the at least one further metal oxide comprises at least titania. It is particularly preferred that the oxide catalyst is $K_2O/TiO_2$ with which catalyst a good conversion has been achieved.

The reaction may be carried out in a batch type reactor or in a continuous flow type reactor. The reaction temperature may be in the range from 300° C. to 450° C., preferably in the range from 360° C. to 390° C.

The weight hourly space velocity WHSV may be in the range of $0.2\ h^{-1}$ to $5.0\ h^{-1}$ depending on the dimensioning of the process parameters. The pressure (absolute) may be in the range of 1.0 bar to 25.0 bar, for example 10±2 bar or 20±2 bar.

The reaction may be carried out in the presence of a carrier gas such as nitrogen, hydrogen, carbon dioxide, $H_2O$ (water vapor) or methane, preferably $H_2$, $CO_2$ or $H_2O$. These gases may be admixed into the reaction mixture and/or may be formed in the course of the reaction. The carrier gas may be used to expel gaseous or volatile reaction products from the product mixture such as $H_2O$ or $CO_2$.

Further, a solvent may be used in the reaction. The reaction does not require the presence of a solvent. If the reaction is carried out in the presence of a solvent, the content thereof is 50 vol-% or less. Further, it is preferable that no solvent is used.

Although it is not desired to be bound to theory, the 5-nonanone production method is generally referred to as a ketonisation reaction. The method provides the benefit that a highly oxygen-deficient product such as 5-nonanone, having an oxygen content of about 11% by weight can be produced from PA, having an oxygen content of about 31% by weight without the need of adding hydrogen gas. Accordingly, it is preferred that no hydrogen gas be added in the ketonisation reaction while forming 5-nonanone from pentanoic acid.

In the method of upgrading according to the present invention, 5-nonanone is generally used as a component of the feedstock. In an alternative embodiment, it is possible that a further ketone such as R1C(O)R2, wherein R1 and R2 may be the same or different and may be alkyl groups, preferably linear alkyl groups, having 1 to 5 carbon atoms; with the provisio that the further ketone is not 5-nonanone is used in addition to or instead of 5-nonanone. When an further ketone is used in addition to 5-nonanone, the content of the further ketone in the feedstock is less than 95 wt.-%, and may be 90 wt.-% or less, 80 wt.-% or less, 70 wt.-% or less, 60 wt.-% or less, 50 wt.-% or less, 40 wt.-% or less, 30 wt.-% or less, 20 wt.-% or less, or 10 wt.-% or less. The further ketone is preferably derived from levulinic acid, further preferably using the method disclosed above. Moreover, the further ketone may be a single ketone for example symmetric or asymmetric or may be mixture of ketones as disclosed above.

According to the 5-nonanone production method, the 5-nonanone is produced with high selectivity of usually more than 95 vol-% and high conversion of usually more than 95 vol-% which eliminates the need for recycling unconverted acid or separation steps. Therefore, it is particularly preferred that no separation other than removal of water and gaseous components be carried out. 5-nonanone spontaneously separates from water. Therefore, in this embodiment, a simple phase separation technique can be used with high efficiency. Separation of water as vapor is a further option.

Conversion of 5-Nonanone to Gasoline, Diesel and/or Jet Fuel Components

In the present invention, the term fuel relates a blend of compounds. Specifically, the fuel of the present invention is a combustion engine fuel, such as a diesel fuel, a gasoline fuel or a jet fuel.

More specifically, the fuel of present invention may be a mixture of compounds, in which the main components, preferably 50 vol-% or more, are hydrocarbons containing 4 to 25 carbon atoms. Diesel fuel may be a mixture of compounds, in which the main components, preferably 50 vol-% or more, are hydrocarbons containing 11 to 25 carbon atoms. Jet fuel may be a mixture of compounds, in which the main components, preferably 50 vol-% or more, are hydrocarbons containing 9 to 16 carbon atoms. Gasoline may be a mixture of compounds, in which the main components, preferably 50 vol-% or more, are hydrocarbons containing 4 to 9 carbon atoms.

In the present invention, 5-nonanone can be further converted by hydrogenation, eventually resulting in hydrocarbon compositions which are suitable as a fuel or as fuel components.

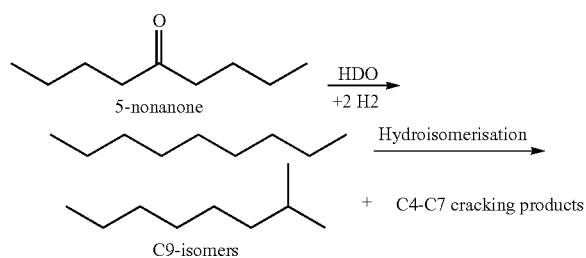

Specifically, the 5-nonanone can be converted to n-nonane using any conventional catalyst, for example sulfide NiMo/alumina hydrotreatment catalyst. Full 5-nonanone HDO to n-nonane can be achieved for example at 240° C. and 40 bars with WHSV=1 and H$_2$/oil ratio 300-500 NL/L or at 265° C. with WHSV=2 or 290 C with WHSV=3. If too severe reaction conditions are used decomposition of ketone to methyl ketone can occur.

5-Nonanone can be combined with triglyceride/fatty acid oils and then subjected to hydrogenated vegetable oil (HVO) type processing like renewable NEXBTL technology invented by Neste Corporation, which technology includes HDO and isomerisation procedures. The product of such a procedure using 5-nonanone as a feedstock is isoparaffinic, similar to a HVO product but having a lower boiling point (C4-C9 isoparaffins) than fatty acid based isoparaffins (C15-C18). Therefore, this fraction derived from 5-nonanone can be easily separated from renewable diesel components derived from the triglyceride/fatty acid oils and is suitable for gasoline and/or JET fuel components. Another beneficial phenomenon is that HDO for producing 5-nonane from 5-nonanone needs much less hydrogen than HDO of triglycerides and therefore produces much less reaction heat. Therefore, 5-nonanone can be used as a dilution agent for plant oils, which create much reaction heat. This means also that product recycle dilution of feed currently introduced can be decreased. This phenomenon increases the efficiency and through put of the HDO process.

Accordingly, the combined use of oil-based e.g. fatty acid oil and fat raw materials and 5-nonanone in a HDO process step provides synergistic effects in that processing control is facilitated and the use of reaction product as a diluent is avoided or reduced while the separation of the products is easy. Such a combination is therefore preferred.

It is also possible to implement partial hydrogenation of 5-nonanone, 5-nonanone conversion to 5-nonanol, which can be also used as fuel component, and have better yield of the product compared to full HDO of 5-nonanone to nonane.

Subsequent isomerization of n-nonane over an isomerization catalyst in the presence of hydrogen gas results in a mixture of branched C4 to C9 alkanes which are suited as fuel components.

The n-nonane can even be used without isomerization, because it itself has good cold properties. Furthermore, it provides excellent cold properties, so that n-nonane is also suitable for use in JET fuel blends.

The cetane number of n-nonane is about 60. Generally, the octane number decreases when chain length of hydrocarbon increases and for C9 molecules the octane number could be even below 0. However, in the experiment, an octane number of 48.4 has been achieved after isomerization. In addition, isomerization improves cold properties and raises the octane number.

The isomerization reaction may be carried out using any conventional isomerization catalyst and is preferably carried out in the presence of hydrogen gas in hydroisomerization. The reaction temperature is preferably in the range of 220° C. to 350° C. depending on the dimensioning of the process parameters. The ratio hydrogen gas/oil in which oil refers to the liquid organic material used as a feed is preferably in the range of 100-500 NL/L depending on the dimensioning of the process parameters. The reaction may be carried out under a pressure (absolute) of 10-80 bar, preferably 15 bar or more, or 20 bar or more, preferably 60 bar or less, or 50 bar or less. The reaction may be carried out in a batch-type reactor or in a flow-type reactor, preferably in a flow-type reactor.

The resulting isomerized hydrocarbon composition may be directly used as a gasoline, diesel and/or jet fuel or may be blended with renewable fuel or with conventional fuel, i.e. fossil fuel or a mixture of fossil fuel components and renewable fuel components such as bio-ethanol. The content of the isomerized hydrocarbon composition in a blend is preferably 10% by weight or more, 20% by weight or more, 30% by weight or more, or 40% by weight or more, and may be up to 100% by weight, or may be 60% by weight or less.

5-Nonanone Condensation

The present invention further relates to the condensation of 5-nonanone for the production of fuel components. The 5-nonanone is preferably produced by the 5-nonanone production process described above. The condensation reaction is preferably a reaction which does not necessarily require the addition of hydrogen and is referred to as an aldol condensation, although it is not desired to be bound to theory.

The condensation reaction may be carried out to condense two or more molecules of 5-nonanone to yield a C18 or a C27 unit. Further reactions in the course of the condensation reaction may cause cracking or oligomerization to give side reaction products e.g. ketones containing 1 oxygen atom and about 18 to 35 carbon atoms, preferably 18 to 27 carbon atoms. Further cracking can lead to alkenes, for example C13 alkenes.

A reaction scheme for a dimerization reaction of 5-nonanone is provided below, showing the main reaction products when employing an ion-exchange resin catalyst:

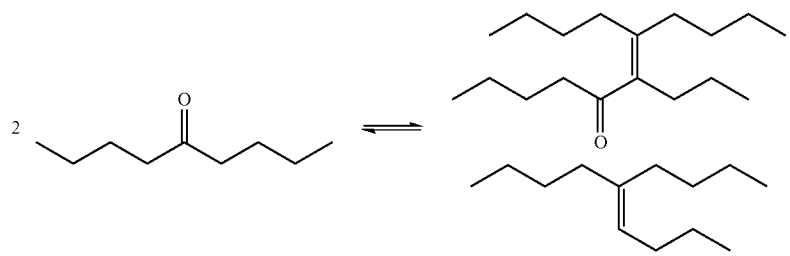

A detailed description of the above reaction scheme is provided in FIG. 1, although it is not desired to be bound to a specific reaction scheme. As can be seen from FIG. 1, dimerisation of 5-nonanone can result in a C18 species having an alcohol group and a keto group. This C18 species can be converted to a C13 olefin e.g. as a diesel fuel component by removal of water and pentanoic acid. This reaction proceeds without hydrogen gas addition. The pentanoic acid can be recycled for producing 5-nonanone, preferably using the method mentioned above. If the C13 olefin is not directly used as a fuel component, it may be subjected to hydrogenation to give a C13 paraffin. In an alternative route, the C18 species can be subjected to water cleavage, which results in a C18 keto-alkene. This keto-alkene may be subjected to hydrogenation (HDO) to yield a C18 paraffin. It is to be noted that the scheme above shows specific compounds, but the skilled person will acknowledge that these schemes encompass isomeric forms of these compounds as well.

The reaction may similarly be carried out using 5-nonanone and any other ketone or further ketone, such as acetone, or any other carbonyl group containing compound, such as LA. However, it is preferred that the reaction mainly results in dimerization and/or oligomerization of 5-nonanone. The higher the content of 5-nonanone, the higher is the probability of a reaction between two or more 5-nonanone molecules. Accordingly, it is preferred that the reaction is carried out with a feedstock comprising at least 5% by weight of 5-nonanone relative to all organic components in the feedstock. The content may be 10% by weight or more, 15% by weight or more, 20% by weight or more, 25% by weight or more, 35% by weight or more, or 45% by weight or more.

Further, since the reaction does not necessarily require a solvent, the content of 5-nonanone in the feedstock may be up to 100% by weight. If the reaction is carried out in the presence of a solvent, the content thereof is preferably less than 50% by weight, less than 30% by weight, less than 20% by weight, less than 10% by weight, or less than 5% by weight relative to all liquid compounds i.e. relative to the feedstock as a whole. It is possible that no solvent is used.

As can be seen from the above reaction scheme, the condensation reaction results in a further decrease of the oxygen content and produces water as the main by-product. Since this reaction does not require the addition of hydrogen, it further contributes to greenhouse gas saving.

Any suitable condensation catalyst may be used to promote the condensation of 5-nonanone. Specific examples of acidic or basic condensation catalysts are an ion-exchange resin catalyst, such as an acidic ion-exchange resin catalyst, a catalyst composed of a basic metal compound, such as a metal hydroxide catalyst or a metal oxide catalyst, a catalyst composed of an acidic metal compound, such as a metal phosphate catalyst or a metal oxide catalyst, a catalyst composed of at least two metal oxides, such as a mixed metal oxide catalyst or a supported metal oxide catalyst.

The catalyst may be a catalyst for homogeneous catalysis or for heterogeneous catalysis.

As the acidic ion-exchange resin catalyst commercially available products may be used, such as Amberlyst-15, 16, 35, 36, 39 or 70. Ion-exchange resin catalysts are usually catalysts for heterogeneous catalysis.

When employing an ion-exchange resin catalyst, the reaction temperature is preferably 80° C. or more, more preferably 90° C. or more, 100° C. or more or 110° C. or more, further preferably 170° C. or less, 160° C. or less, 140° C. or less, or 130° C. or less. Using moderate reaction temperatures allows the production of high molecular weight reaction products e.g. "dimers" of 5-nonanone while reducing the risk of undesired side reactions. The reaction may be conducted at a pressure of 0.2-100.0 bar, preferably 0.5-50.0 bar, more preferably 1.0-20.0 bar. The weight hourly space velocity (kg feedstock/kg catalyst*h) may be in the range of 0.05 $h^{-1}$ to 2.00 $h^{-1}$, preferably 0.10 $h^{-1}$ to 1.50 $h^{-1}$, more preferably 0.15 $h^{-1}$ to 1.00 $h^{-1}$, most preferably 0.20 $h^{-1}$ to 0.75 $h^{-1}$.

The base catalyst may be any conventional base catalyst, e.g. a catalyst for homogeneous catalysis or for heterogeneous catalysis, and may include metal hydroxides, such as NaOH, KOH, or $Ca(OH)_2$, a metal oxide, such as CaO, a metal alkoxide, such as $NaOCH_3$, or a metal salt, such as $K_2CO_3$. The metal hydroxide catalysts and the metal alkoxide catalysts are mainly employed for homogeneous catalysis, although not being limited thereto. When employing a base catalyst, the reaction temperature is preferably 70° C. or more, 80° C. or more, 90° C. or more or 100° C. or more, further preferably 195° C. or less, 160° C. or less, 140° C. or less or 120° C. or less. In this case, it is preferred that water be contained in the reaction mixture before initiation of the reaction, preferably in an amount of 2 to 30% by weight relative to all liquid components of the reaction mixture, but it is possible that no water is present. An alcohol, such as methanol, ethanol or propanol, may be present instead of in addition to water in an amount of 2 to 30% by weight relative to all liquid components of the reaction mixture. The base may be a hydroxide, carbonate, or phosphate of an alkaline metal or alkaline earth metal, preferably a hydroxide, carbonate, or phosphate of one of Na, Li, Be, Mg, K, Ca, Sr or Ba, or a combination of these, more preferably sodium hydroxide, potassium hydroxide or lithium hydroxide or a combination of these.

The oxide catalyst such as metal oxide catalyst may be any conventional one and may be an acidic oxide catalyst, for example a tungsten oxide-based catalyst e.g. $WO_3$, and is preferably a metal oxide catalyst comprising at least two different metal oxides as a mixture, including the case where one metal oxide is supported on another metal oxide, as a mixed oxide or as a solid solution. The metal oxide catalyst is preferably a solid metal oxide catalyst for heterogeneous catalysis. Examples of a mixed metal oxide catalyst include $MgO.Al_2O_3$ (basic), $SiO_2.Al_2O_3$ (acidic), and examples of a supported metal oxide catalyst include $K/Al_2O_3$ (basic) and $WO_3/ZrO_2$ (acidic).

When employing a metal oxide catalyst, the reaction temperature may be 70° C. or more, preferably 80° C. or more, 90° C. or more, 110° C. or more, 130° C. or more, 150° C. or more, 180° C. or more, or 200° C. or more, further preferably 300° C. or less, 280° C. or less, 250° C. or less or 240° C. or less. In the case of using a metal oxide catalyst comprising two metal oxides i.e. two metal oxides being different from each other, any combination of two or more oxides can be chosen from oxides of Be, B, Mg, Al, Si, P, Ca, Sc, Ti, V, Cr, Mn, Fe, Co, Ni, Cu, Zn, Ga, Ge, Sr, Y, Zr, Nb, Mo, Cd, Sn, Sb, Ba, W, Re, Bi, La, or Ce. The reaction may be conducted at a pressure of 0.5-100 bar, preferably 1.0-50 bar, more preferably 1.0-20 bar. The weight hourly space velocity (kg feedstock/kg catalyst*h) may be in the range of $0.05\ h^{-1}$ to $2.0\ h^{-1}$, preferably $0.1\ h^{-1}$ to $1.8\ h^{-1}$, more preferably $0.2\ h^{-1}$ to $1.5\ h^{-1}$, most preferably $0.25\ h^{-1}$ to $1.25\ h^{-1}$.

The reaction may be carried out in a batch-type reactor or in a continuous flow type reactor.

The reaction may be carried out under flow of a carrier gas, such as nitrogen, hydrogen, carbon dioxide, methane or water. A flow of carrier gas may increase the total conversion rate of 5-nonanone. In particular when preparing diesel fuels, the most desirable product of the condensation reaction is the C18 dimerization product, so that the flow of carrier gas should be kept low, preferably below 10.0 NL per L feedstock, more preferably below 5.0 NL/L, below 2.0 NL/L, below 1.0 NL/L, below 0.5 NL/L, or below 0.3 NL/L, but may be above 0 NL/L, preferably above 0.05 NL/L. It is also possible to use no carrier gas.

Furthermore, it is to be noted that the condensation reaction of the present invention does not consume hydrogen gas, but nevertheless further reduces the oxygen content of the organic material. That is, in the case of producing a dimerization product such as C18 product shown in the above scheme, the product has an oxygen content of about 7% by weight whereas the raw material (5-nonanone) has an oxygen content of about 11% by weight.

In view of greenhouse gas saving, it is thus preferred that no hydrogen gas is added to the reaction mixture in condensation reaction step. On the other hand, low amounts of hydrogen gas may increase catalyst stability, especially in the case of using an acidic ion-exchange resin catalyst, so that the addition of low amounts of hydrogen for increasing the catalyst stability may be beneficial.

In any case, the condensation reaction of the present invention is a condensation reaction in which 5-nonanone is directly condensed. In other words, the 5-nonanone is not converted to 5-nonanol or an alkene e.g. by hydrogenation before the C—C-bond forming reaction such as oligomerization of olefins.

The raw product of the condensation reaction may be purified to remove unreacted components as well as water and gaseous and/or volatile components to obtain the condensation product with higher selectivity and conversion.

Use of Condensation Product and Fuel Comprising the Condensation Product

The 5-nonanone condensation product of the method of the present invention is highly oxygen-depleted while only a minimum amount of hydrogen is consumed in the course of the production process.

In order to maintain this excellent greenhouse gas saving effect, the 5-nonanone condensation product, usually a mixture of C18 ketone, optionally C13 olefin and low amounts of other components can be directly used as a fuel component without being hydrogenated.

Accordingly, the present invention further provides a use of the condensation product as a fuel component, preferably as a fuel component in a diesel fuel blend and/or a jet fuel blend, and a fuel blend, preferably a diesel fuel blend and/or a jet fuel blend, comprising the condensation product.

The content of the condensation product in the fuel blend may be 2% by weight or more, preferably 5% by weight or more, 10% by weight or more, 15% by weight or more, or 20% by weight or more, preferably 50% by weight or less, 40% by weight or less, 30% by weight or less, or 25% by weight or less.

Hydrogenation of Condensation Product, Use of the Hydrogenated Condensation Product and Fuel Comprising the Hydrogenated Condensation Product In order to further improve the properties or compatibility of the condensation product as a fuel component, the condensation product may be subjected to a hydrogenation reaction. For example, cetane number will increase when the alkene such as C13 alkene is converted to corresponding paraffin. When combined with other methods of the present application, the overall process starting out from LA as a renewable source may be summarized as follows:

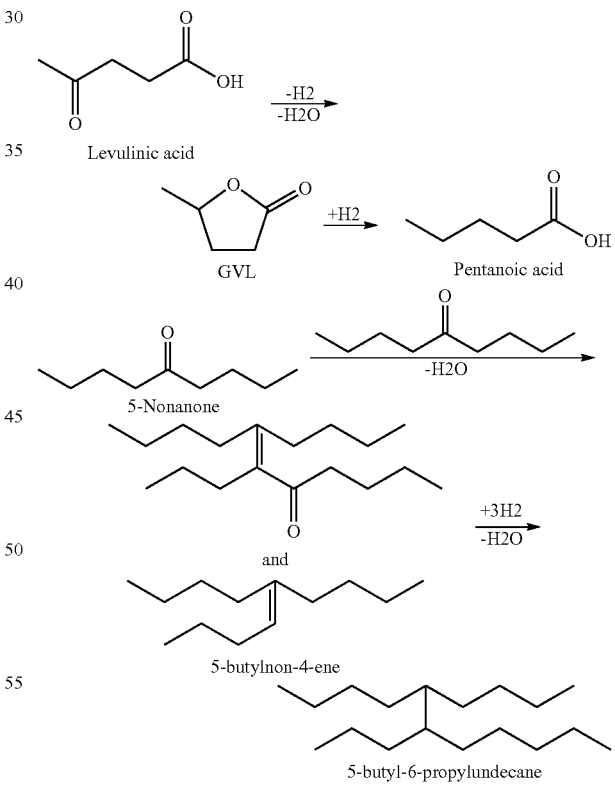

The hydrogenation reaction may be a reaction for selectively removing a double bond which is present in the condensation product e.g. in the C18 or C13 condensation product, a reaction for selectively removing a keto group which is present in the condensation product, or a full hydrogenation thus producing an alkane/paraffin composition. Any of these hydrogenation treatments may be a single step hydrogenation or a multi-step, preferably 2-step hydrogenation. Especially in the case of a full hydrogenation, it may be beneficial to employ a multi-step (2-step) process.

Any known method employing any known catalyst may be used for hydrogenating or hydrodeoxygenating the condensation product. Preferably, the hydrogenation catalyst comprises a hydrogenation metal on a support, such as for example a hydrogenation or HDO catalyst metal selected from a group consisting of Pd, Pt, Ni, Co, Mo, Ru, Rh, W or any combination of these. For example, a sulfided NiMo catalyst may be used in the hydrogenation reaction.

The hydrogenation may be conducted at a temperature in the range of 100-500° C., preferably 250-380° C., and at a pressure in the range of 10-150 bar, preferably 30-80 bar.

The present invention further provides a use of the hydrogenated condensation product as a fuel component, preferably as a fuel component in a diesel fuel blend, and a fuel blend, preferably a diesel fuel blend, comprising the hydrogenated condensation product.

The content of the hydrogenated condensation product in the fuel blend is not particularly limited and may be 5% by weight or more, preferably 10% by weight or more, 20% by weight or more, 25% by weight or more, 30% by weight or more, 40% by weight or more, 50% by weight or more, 60% by weight or more, 70% by weight or more, 80% by weight or more, 90% by weight or more, 95% by weight or more, or 99% by weight or more.

EXAMPLES

The present invention is further illustrated by way of Examples. However, it is to be noted that the invention is not intended to be limited to the exemplary embodiments presented in the Examples.

Example 1

In n-nonane isomerization experiment it was tested, if isomerization treatment of n-nonane could improve the fuel properties. Conditions during test run of isomerization of n-nonane to i-nonanes in a flow-type reactor were: conventional isomerization catalyst as a catalyst, initial reactor temperatures 310° C. and 330 C, respectively, pressure 40 bar, feed WHSV 0.4 h$^{-1}$ and hydrogen/oil ratio 300 NL/L.

TABLE 1

Results for n-nonane isomerization

| Temp. ° C. | n-nonane conversion, wt-% | Unreacted n-C9 product, wt-% | C9 isomers in product, wt-% | Cetane number | Octane number | Cloud point ° C. |
|---|---|---|---|---|---|---|
| 310 | 83.7 | 16.3 | 81.9 | 51.2 | | <-95 |
| 330 | 90.2 | 9.8 | 85.0 | | 48.4 | |

In the present invention, the relative contents (wt.-%) of materials in a liquid mixture/in a liquid blend can be determined from the GC area in GC-MS analysis.

The conversion of n-nonane to i-nonanes increases with increasing temperature. Temperature increase from 310° C. to 330° C. increased the conversion from 84% to 90%.

The isomerized product (330° C.) was analysed for detailed composition by GC feed chromatogram. The product had 16.7 wt-% n-paraffins and 82.8 wt-% i-paraffins. The product composition had 26% 4-methyl-octane, 25% 3-methyl-octane, 16% 2-methyl-octane, 16% n-nonane, 7% 3,5-dimethyl-heptane, 4% 2,6-dimethyl-heptane, 3% 2,3-dimethyl-heptane, 2% dimethyl-heptane and 3% other components.

The cetane number of n-nonane is about 60 while the cetane number of the test component after isomerization (310° C.) was decreased to 51.2 during isomerization. The octane number of the component after isomerization (330° C.) was measured to be 48.4. Generally the octane number decreases when chain length increases and for C9 molecules the octane number could be even below 0. However, in the experiment, an octane number of 48.4 has been achieved.

Example 2

5-nonanone was subjected to aldol condensation under various conditions, thus forming mainly dimers and trimers from the C-9 ketone. The dimers and trimers from 5-nonanone have potential as diesel fuel components.

The 5-nonanone condensation tests were done in a flow-type reactor using the following conditions: Amberlyst 36 as a catalyst, temperature 120° C., WHSV 0.22 h$^{-1}$, ambient pressure.

Figure 2:
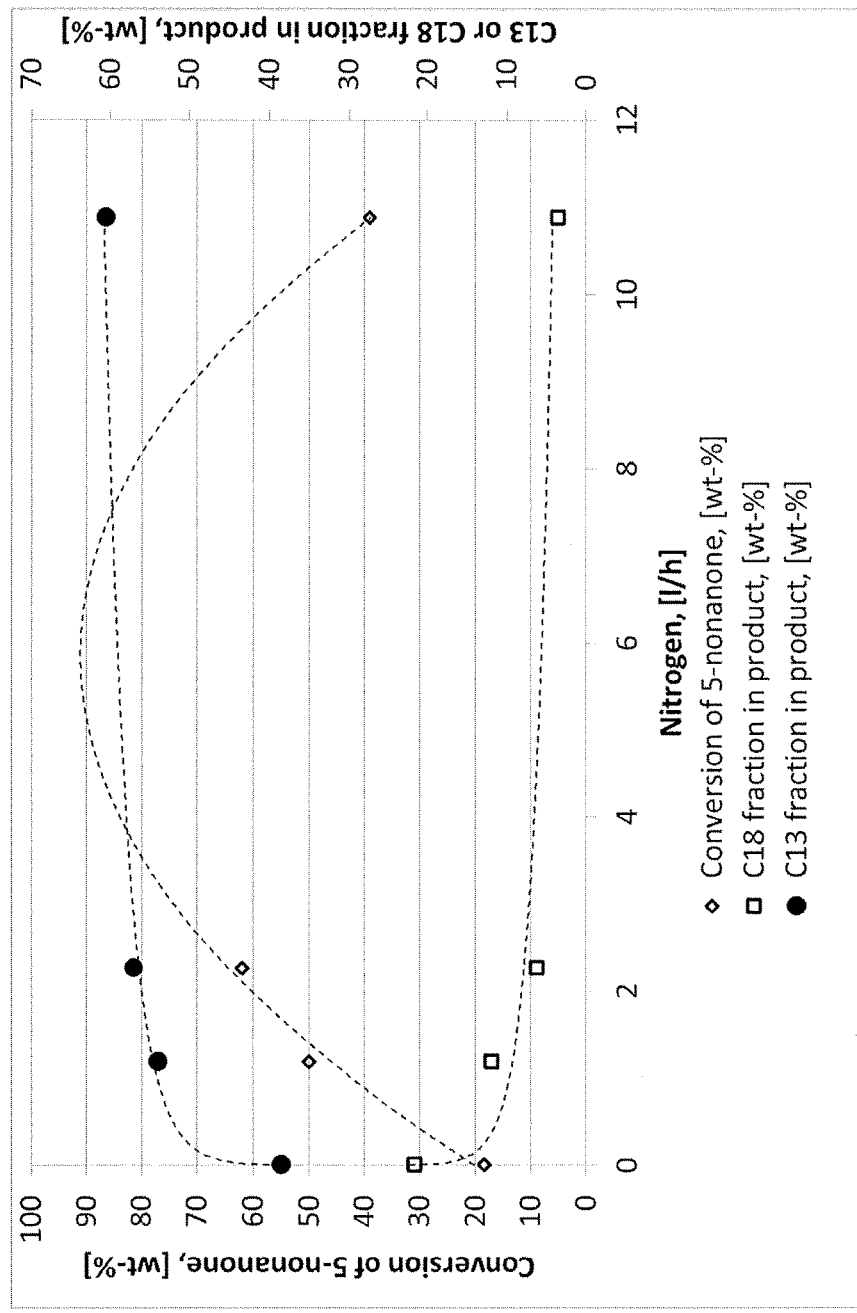
FIG. 2 is a diagram showing influence of the nitrogen flow rate on 5-nonanone conversion and dimer product formation in a method of upgrading 5-nonanone in accordance with the present invention.

Nitrogen was used as a carrier gas and flow levels of 0 L/h, 1 L/h, 2 L/h, and 11 L/h were tested. In the absence of nitrogen flow (0 L/h), low conversion of 5-nonanone was observed. An increase of the nitrogen flow rate to 2 L/h significantly increased the conversion. However, the product distribution was not improved. The most wanted product is the C18 dimer product. Generally, it was found that increasing the nitrogen flow rate decreases the amount of the dimers fraction in the product. The total product distribution is shown in Table 2. The relationship between nitrogen flow rate and 5-nonanone conversion and dimer product formation is shown in FIG. 2.

TABLE 2

Results of aldol condensation of 5-nonanone

| Gas flow, [L/h] | Temperature [° C.] | Gauge Pressure [bar] | 5-nonanone conversion % | Product Selectivity wt-% | | |
|---|---|---|---|---|---|---|
| | | | | C18 | <C18 (mostly C13 and C5) | >C18 |
| 0 | 119 | 0 | 15 | 22 | 67 | 12 |
| 1 | 122 | 0 | 41 | 12 | 74 | 14 |
| 2 | 122 | 0 | 54 | 6 | 80 | 13 |
| 11 | 122 | 0 | 32 | 4 | 86 | 11 |

5-nonanone conversion increased when a small amount of nitrogen was introduced. With a high nitrogen flow, the conversion drops again. Besides C18 dimers, cracked C13 fraction and C5 (pentanoic acid) are formed.

Example 3

Aldol condensation of 5-nonanone was carried out in a batch reactor over different catalysts with and without N$_2$ as a carrier gas. The specific reaction conditions are shown in Table 3 below. The influence of the reaction conditions on the formation of 5-nonanone dimers was evaluated.

TABLE 3

Aldol condensation in batch reactor - reaction conditions

| Entry | Feed | Catalyst | Reaction temp. [° C.] | N2 gas flow through [L/h] |
|---|---|---|---|---|
| 1 | 5-nonanone | | Amberlyst-36 | 120 | 10 |
| 2 | 5-nonanone | | Amberlyst-36 | 120 | — |
| 3 | 5-nonanone | | NaOH | 120 | — |
| 4 | 5-nonanone | | La—ZrOx | 120 | 10 |
| 5 | 5-nonanone (75%) | Acetone (25%) | Amberlyst-36 | 120 | — |
| 6 | 5-nonanone (75%) | Levulinic acid (25%) | Amberlyst-36 | 120 | — |

Liquid chromatographic (LC)-analysis results from the experiment with 5-nonanone as feed over Amberlyst-36 catalyst at a reaction temperature of 120° C. with nitrogen gas 10 L/h flowing through the reactor (Entry 1) or without nitrogen gas (Entry 2) are shown in Tables 4 and 5 below, respectively. After 24 h, the conversion under nitrogen flow was 46.3% and the main reaction products were products smaller than dimers (<C18).

TABLE 4

Conversion of 5-nonanone and reaction products (Entry 1). Pentanoic acid, C13-olefins and 5-nonanone dimers/higher oligomers were detected.

| Compound | 5-nonanone conversion % | Product selectivity wt-% |
|---|---|---|
| Time h | | 24 h |
| 5-nonanone | 46.3 | |
| Dimers C18 | | 21.2 |
| Smaller than dimers <C18 | | 65.9 |
| Larger than dimers >C18 | | 12.9 |

TABLE 5

Conversion of 5-nonanone and reaction products (Entry 2).

| Compound | 5-nonanone conversion % | Product selectivity wt-% |
|---|---|---|
| Time h | | 21.5 h |
| 5-nonanone | 19.7 | |
| Dimers C18 | | 46.4 |
| Smaller than dimers <C18 | | 38.3 |
| Larger than dimers >C18 | | 15.3 |

According to the results it was possible to increase the conversion of 5-nonanone by passing nitrogen gas through the reactor system and thereby shifting the equilibrium towards the products.

In the experiment with levulinic acid and 5-nonanone (Entry 6), the conversion stayed low. After a reaction time of 23 h the 5-nonanone conversion was about 20%.

Further, the conversion of 5-nonanone was low also in the experiment where 5-nonanone was reacted over La/ZrO$_x$ (Entry 4) even after a reaction time of 24 h. The area-% (wt.-%) of 5-nonanone was about 96% when analyzing the product with GC-MS. When acetone was allowed to react with 5-nonanone over Amberlyst-36 catalyst (Entry 5), small amounts of products were detected with GC-MS.

Example 4

The 5-nonanone aldol condensation product produced in a batch reactor (table 4 from example 3) was subjected to HDO over NiMo catalyst at temperature of 310° C., a pressure of 60 bar and a reaction time of 20 h, in order to remove the oxygen from the product mixture. The end product was analysed with GC-MS. The properties of the sample can be seen in Table 6. The structures of HDO products were characterized with GC-MS; cf. Table 7 below.

TABLE 6

Product properties

| Analyzed property | Analysis results |
|---|---|
| Density [kg/m3] | 749.5 |
| Cloud point [° C.] | −71.0 |

TABLE 7

Products detected with GC-MS

| Product | Area-% |
|---|---|
| n-nonane | 27 |
| C13-isoparaffins and -olefins | 50 |
| C18 isoparaffins | 7 |
| Others | 16 |

Example 5

The 5-nonanone aldol condensation product produced in flow type reactor (Example 2) was subjected to HDO conditions over NiMo catalyst at 320° C. at 50 bar hydrogen pressure for 48 h. The end product properties can be seen in Table 8 below.

TABLE 8

Product properties of 5-nonanone aldol condensation product after HDO conditions.

| Analysed property | Analysis result |
|---|---|
| Density [kg/m3] | 769.4 |
| Cloud point [° C.] | −68.4 |
| Cetane number | 50 |

The structures of the HDO products were characterized with GC-MS (Table 9).

TABLE 9

Products identified with GC-MS.

| Product | Area-% |
|---|---|
| n-nonane & nonene | 49 |
| Nonanone | 8 |
| C13-isoparaffins and -olefins | 26 |
| Heavy compounds (ketones, aromatics, olefins, paraffins) | 9 |
| Others | 8 |

The product distribution according to boiling point was determined by SimDist (ASTM D2887) analysis (Table 10)

TABLE 10

SimDist analysis of HDO end product.

| Boiling point [° C.] | Recovered mass-% | Fraction mass-% |
|---|---|---|
| 50 | 0.2 | 0.2 |
| 170 | 48.5 | 48.3 |
| 221 | 63.4 | 14.9 |
| 360 | 94.1 | 30.7 |

The invention claimed is:

1. A method for producing fuel components, the method comprising:
   providing a feedstock having at least 5 wt.-% of 5-nonanone; and
   condensing at least the 5-nonanone in the feedstock in the presence of a condensation catalyst to obtain a condensation product,
   wherein the condensing results in dimerization of 5-nonanone and/or oligomerization of 5-nonanone, and/or condensation of 5-nonanone with a further ketone.

2. The method according to claim 1, wherein no hydrogenation is carried out in the condensing.

3. The method according to claim 1, wherein the condensation catalyst is:
   i) an ion-exchange resin catalyst;
   ii) an acid or a base catalyst selected from the group of a metal oxide catalyst, a metal hydroxide catalyst, a metal alkoxide catalyst, metal carbonate catalyst or a metal phosphate catalyst; or
   iii) a mixed metal oxide catalyst or a supported metal oxide catalyst.

4. The method according to claim 1, wherein the condensing is carried out under flow of a carrier gas.

5. The method according to claim 1, comprising:
   hydrogenating the condensation product to obtain a hydrogenated condensation product.

6. The method according to claim 5, wherein the hydrogenated condensation product is a hydrocarbon composition.

7. A condensation product obtained by the method according to claim 1.

8. A diesel, jet or gasoline fuel blend comprising:
   the condensation product obtained by the method according to claim 1.

9. The method according to claim 2, wherein the condensation catalyst is:
   i) an ion-exchange resin catalyst;
   ii) an acid or a base catalyst selected from the group of a metal oxide catalyst, a metal hydroxide catalyst, a metal alkoxide catalyst, metal carbonate catalyst or a metal phosphate catalyst; or
   iii) a mixed metal oxide catalyst or a supported metal oxide catalyst.

10. The method according to claim 9, wherein the ion-exchange resin catalyst is an acidic ion-exchange resin catalyst.

11. The method according to claim 4, wherein the carrier gas is nitrogen, hydrogen, carbon dioxide, methane or water.

12. The method according to claim 10, wherein the condensing is carried out under flow of a carrier gas.

13. The method according to claim 12, comprising:
   hydrogenating the condensation product to obtain a hydrogenated condensation product.

14. The method according to claim 13, wherein the hydrocarbon composition is an alkane or a mixture of alkanes.

15. A hydrogenated condensation product obtained by the method of claim 5.

16. A hydrogenated condensation product obtained by the method according to claim 5.

* * * * *